United States Patent
Mongeon

(10) Patent No.: US 7,712,467 B2
(45) Date of Patent: May 11, 2010

(54) ARTIFICIAL AIRWAY DEVICE AND METHOD OF ITS USE

(75) Inventor: Douglas R. Mongeon, Orange Park Acres, CA (US)

(73) Assignee: Vital Signs, Inc., Totowa, NJ (US)

( * ) Notice: Subject to any disclaimer, the term of this patent is extended or adjusted under 35 U.S.C. 154(b) by 2003 days.

(21) Appl. No.: 10/437,714

(22) Filed: May 13, 2003

(65) Prior Publication Data

US 2003/0192552 A1    Oct. 16, 2003

Related U.S. Application Data

(60) Division of application No. 09/589,499, filed on Jun. 7, 2000, now abandoned, which is a continuation-in-part of application No. 09/291,715, filed on Apr. 14, 1999, now Pat. No. 6,390,093.

(51) Int. Cl.
*A61M 16/00*    (2006.01)
*A61M 15/00*    (2006.01)

(52) U.S. Cl. ............... 128/207.14; 128/200.26; 128/200.24

(58) Field of Classification Search ........... 128/200.24, 128/200.26, 205.19, 207.14, 207.15, 206.29; 604/174; 600/532
See application file for complete search history.

(56) References Cited

U.S. PATENT DOCUMENTS

| | | | | |
|---|---|---|---|---|
| 2,677,375 A | * | 5/1954 | Raiche | .................. 604/96.01 |
| 4,265,621 A | * | 5/1981 | McVey | .................. 433/91 |
| 4,509,514 A | | 4/1985 | Brain | |
| 4,995,388 A | * | 2/1991 | Brain | .................. 128/207.15 |
| 5,015,184 A | * | 5/1991 | Perry et al. | .................. 433/93 |
| 5,078,603 A | * | 1/1992 | Cohen | .................. 433/91 |
| 5,241,956 A | | 9/1993 | Brain | |
| 5,249,571 A | | 10/1993 | Brain | |
| 5,282,464 A | | 2/1994 | Brain | |
| 5,297,547 A | | 3/1994 | Brain | |
| 5,305,743 A | | 4/1994 | Brain | |
| 5,322,062 A | | 6/1994 | Servas | |
| 5,355,879 A | | 10/1994 | Brain | |
| 5,443,063 A | | 8/1995 | Greenberg | |
| 5,499,625 A | | 3/1996 | Frass et al. | |
| 5,513,627 A | | 5/1996 | Flam | |
| 5,584,290 A | | 12/1996 | Brain | |
| 5,623,921 A | * | 4/1997 | Kinsinger et al. | ...... 128/200.26 |
| 5,632,271 A | | 5/1997 | Brain | |
| 5,653,229 A | | 8/1997 | Greenberg | |
| 5,682,880 A | | 11/1997 | Brain | |
| 5,791,341 A | | 8/1998 | Bullard | |

(Continued)

FOREIGN PATENT DOCUMENTS

GB    2 323 291    9/1998

*Primary Examiner*—Steven O Douglas
*Assistant Examiner*—Annette F Dixon
(74) *Attorney, Agent, or Firm*—Kenyon & Kenyon LLP

(57) ABSTRACT

An artificial airway device comprises an air conduit extending between a proximal opening and a mask opening. When the device is in an operative position, the proximal opening remains outside of a patient and the mask opening is open to a laryngeal opening of the patient. The device further includes a seating tip extending distally from the distal end of the airway tube which, when the device is in the operative position, is located on a pharyngeal side of the patient's cricoid.

7 Claims, 7 Drawing Sheets

U.S. PATENT DOCUMENTS

| | | |
|---|---|---|
| 5,871,012 A | 2/1999 | Neame et al. |
| 5,937,859 A * | 8/1999 | Augustine et al. ...... 128/207.15 |
| 6,119,695 A * | 9/2000 | Augustine et al. ...... 128/207.15 |
| 6,152,136 A * | 11/2000 | Pagan .................... 128/207.15 |
| 6,196,224 B1 | 3/2001 | Alfery |
| 6,240,922 B1 * | 6/2001 | Pagan .................... 128/207.15 |
| 6,318,367 B1 | 11/2001 | Mongeon |
| 6,386,199 B1 | 5/2002 | Alfery |
| 6,390,093 B1 * | 5/2002 | Mongeon ............... 128/207.15 |
| 6,705,318 B1 * | 3/2004 | Brain .................... 128/207.14 |
| 7,040,312 B2 * | 5/2006 | Alfery et al. ........... 128/200.26 |

* cited by examiner

ARTIFICIAL AIRWAY DEVICE AND METHOD OF ITS USE

RELATED APPLICATIONS

This is divisional application of U.S. Ser. No. 09/589,499, filed Jun. 7, 2000, now abandoned which is a continuation-in-part of U.S. Ser. No. 09/291,715, filed Apr. 14, 1999 now U.S. Pat No. 6,390,093.

BACKGROUND OF THE INVENTION

1. Field of the Invention

The present invention relates to artificial airway devices used to facilitate lung ventilation in unconscious patients, and more specifically to devices designed for placement above the laryngeal opening of the patient in order to prevent airway obstruction and to permit either spontaneous or controlled ventilation.

2. Description of Related Art

To maintain open the airway of an unconscious patient under general anesthesia, it is common practice to use an endotracheal tube, which is a flexible tube of rubber or plastic which is inserted down through the trachea. Prior art endotracheal tubes frequently include an inflatable cuff disposed symmetrically around a distal end of the tube, which distal end is inserted into the trachea. The inflatable cuff is used to seal and secure the endotracheal tube in place.

Typically, the endotracheal tube is introduced through mouth or nose and the larynx into the trachea or windpipe, and then the cuff is inflated through a small auxiliary tube in order to form a seal against the wall of the trachea. Introduction of the endotracheal tube into a patient is a skilled operation normally requiring use of a laryngoscope to guide the tube through the larynx, past the vocal cords and into the trachea. Intubation using an endotracheal tube is difficult or even impossible in some patients. Moreover, there is a significant risk of damage to soft tissues or to the larynx when using an endotracheal tube. Likewise, there is a risk of accidental, but highly undesirable, intubation of the esophagus or of the right or left main bronchus when using an endotracheal tube.

Alternatively, oro- or naso-pharyngeal airway devices may be used to maintain open the airway of a patient under general anesthesia. An oro- or naso-pharyngeal airway is a flexible tube extending from the mouth (oro-pharyngeal airway) or nose (naso-pharyngeal airway) into the patient's pharynx but not into the patient's larynx. An oro- or naso-pharyngeal airway is normally used in conjunction with a face mask over the patient's mouth and/or nose, unlike an endotracheal tube, which normally is not used with a mask. While preventing obstruction of the airway by the tongue, an oro- or nas-opharyngeal airway device cannot be used conveniently for controlled ventilation of the patient and does not prevent inhalation of extraneous matter (i.e., aspiration). For these and other reasons this type of device is less desirable in many applications.

Prior art artificial airways (see for example, U.S. Pat. Nos. 4,509,514; 4,995,388; 5,241,956; 5,249,571; 5,282,464; 5,297,547; 5,305,743; 5,355,879; 5,584,290; 5,632,271 and 5,682,880 to Archibald I. J. Brain—collectively, the "Brain patents") use a curved tube and a laryngeal mask portion at one end of the tube. The mask portion includes a flexible annular inflatable collar which surrounds a hollow interior space of the mask portion. The mask portion is pre-formed with a roughly elliptical shape which is purported to be capable of conforming to, and fitting within, the space behind the larynx to form a seal around the circumference of the laryngeal inlet without penetrating into the interior of the larynx. The curved tube opens into the mask portion and provides an airway with the axis of the tube substantially aligned with the length of the elliptical formation of the mask portion.

In the Brain patents, the curved tube opens into a lumen of the mask through an aperture which is provided with flexible cross-bars to prevent the aperture from being obstructed by the epiglottis, while permitting passage of a second smaller tube, such as an endotracheal or endobronchial tube, a suction catheter, or an inspection tube such as a fiber-optic broncho- or laryngoscope.

SUMMARY OF THE INVENTION

The present invention is directed to an artificial airway device comprising an air conduit extending between a proximal opening and a mask opening. When the device is in an operative position, the proximal opening remains outside of a patient and the mask opening is open to a laryngeal opening of the patient. The device further includes a seating tip extending distally from the distal end of the airway tube which, when the device is in the operative position, is located on a pharyngeal side of the patient's cricoid.

The artificial airway device is designed to overcome certain shortcomings which have been discovered with the use, in practice, of artificial airways of the prior art. The present invention is also designed to be inexpensive, to be easy to insert without causing damage to the patient and without the need for a laryngoscope or other inspection instruments, and to provide an effective airway which is not readily blocked or obstructed during use.

The present invention is inexpensive to use and easy to insert and therefore appropriate for Emergency Medical Service (EMS) use. This provides advantages over the prior art; the airway devices as shown in the Brain patents can have a tendency for the uninflated collar to pleat or fold during insertion, which results in incomplete expansion of the collar during inflation. Incomplete inflation results in leakage, which prevents effective use of the artificial airway in the manner in which it is intended to be used. Furthermore, the inflatable collars often do not conform well to the airway, also resulting in leakage. In addition, it is often difficult for the individual inserting the artificial airways shown in the Brain patents to determine whether the inflatable collar is completely inflated. In order to overcome these inflation and leakage problems, artificial airways with inflatable collars are often overinflated by the individual inserting the airway to pressures sufficiently high that they can cause damage to the soft tissue against which the inflatable collar seals.

Another difficulty with prior art artificial airways using an inflatable collar, as in the Brain patents, is that it is often difficult for the individual inserting the airway to determine when the airway mask is properly in place over the larynx. This uncertainty of proper placement makes complete sealing more difficult, and also complicates insertion of the airway into the patient. Because of this difficulty, the artificial airways of the Brain patents are generally not suitable for EMS use. Additionally, artificial airways with inflatable collars, because they must be completely inflated to properly seal, require a large number of sizes to accommodate the different sizes of airways of the patients to which they are administered. Endotracheal tubes and oro- or nas-opharyngeal airways are also generally not suitable for use by EMS personnel.

Prior art artificial airways can also cause difficulties in ensuring that the artificial airway, or parts of the airway, does not accidentally enter the esophagus during insertion. Entry into the esophagus can cause damage to delicate tissues, which is undesirable and can cause severe complications for the patient. Furthermore, the prior art artificial airways often do not have adequate mechanisms to securely anchor the device in place after insertion, a feature which is important, particularly in EMS use.

The present invention is an artificial airway device used to facilitate lung ventilation in an unconscious patient and methods for using and inserting an artificial airway device, all of which overcome the shortcomings of prior art artificial airway devices. The device of the present invention includes a curved but flexible airway tube and a mask portion, which mask portion includes a mask opening portion and a seating tip. The mask portion is attached to the airway tube at a distal end of the airway tube. The mask opening portion is shaped so as to fit closely adjacent and closely over the patient's laryngeal opening without entering into the larynx and without requiring the mask opening portion to be sealed against the larynx or laryngeal opening. The seating tip includes a series of thin, flexible fins or gills which project from a relatively rigid projecting finger extending axially from, and preferably formed integrally with, the mask opening portion. On one side of the seating tip, at least some of the fins or gills can have an undulating shape across their width, in one embodiment of the invention, to compensate for flexing or expansion of the seating tip as it seats in position. The fins or gills seat against the pharyngeal side of the cricoid, just above the esophagus. In this way, the mask can be properly located above the laryngeal opening, and can be anchored against a relatively hard surface without causing damage to delicate tissue in the esophagus or delicate tissue in or around the larynx or laryngeal opening. The seating tip, and its placement against the pharyngeal side of the cricoid, therefore provides a reference for the person inserting the artificial airway device which ensures that the mask opening portion is properly in place and adequately anchored or seated in place. The interaction between the seating tip and the pharyngeal side of the cricoid helps ensure that the individual inserting the airway accurately positions the mask opening portion, and therefore the connection to the airway tube, over the patient's laryngeal opening. The pharyngeal side of the cricoid also serves as a relatively rigid anchoring area for the mask portion, thereby ensuring that the mask opening portion remains in position closely adjacent and closely surrounding the laryngeal opening. The mask opening portion is shaped to conform to the space around the laryngeal opening, thereby providing an airway to the laryngeal opening without having to form a seal around the circumference of the laryngeal opening and without penetrating into the interior of the larynx or the entrance to the esophagus.

The shape of the mask opening portion ensures that it closely approximates the shape of the laryngeal opening. Because the artificial airway of the present device is not required to seal against the laryngeal opening, and because the seating tip of the present invention is designed to anchor or seat against the relatively rigid pharyngeal side of the cricoid, only a few artificial airway sizes are needed to accommodate a wide range of patient airway sizes, therefore reducing the number of artificial airway sizes needed. This feature of the present invention also reduces costs, and makes the present invention more amenable to EMS use, since fewer devices, and less storage space, is needed by the EMS crew. In addition, the seating of the seating tip against the pharyngeal side of the cricoid provides a good tactile indication when the mask opening portion is properly in place in the airway, thereby enhancing the ease and accuracy of insertion of the artificial airway in the patient.

The artificial airway of the present invention is designed to be easy and convenient to insert in the majority of patients. The artificial airway may also be inexpensively manufactured in quantity, thereby allowing it to be disposable. As a result, the artificial airway of the present invention may be more readily used in EMS or other non-hospital applications, as well as in surgical applications. When the seating tip of the mask portion reaches the pharyngeal side of the cricoid above the esophagus, a definite end-point can be felt by the individual inserting the artificial airway, indicating that the mask portion is correctly placed. The mask portion does not enter the larynx or trachea, and the seating tip does not enter the esophagus, so the risk of damage to these delicate structures is avoided.

Likewise, the risk of accidental entry of the mask portion into the esophagus or one of the main bronchi is also avoided with use of the artificial airway of the present invention. Once in place, the artificial airway is generally used to allow the lungs to be ventilated by positive pressure. Alternatively, the patient may be permitted to breathe spontaneously after insertion of the artificial airway of the present invention.

The seating tip of the present invention may provide some degree of blockage so as to prevent gastric reflux from the stomach and aspiration into the patient's airway, making the artificial airway of the present invention more adaptable to emergency and EMS use, as well as adaptable to a larger variety of surgical applications than prior art artificial airways.

The present invention also includes an inflatable cuff used to anchor the artificial airway in place using the patient's tongue and oro-pharynx behind the uvula. This inflatable cuff is preferably offset relative to the airway tube. The offset of the inflatable cuff helps to ensure that the mask opening portion is held closely near the laryngeal opening, thereby allowing more effective operation of the artificial airway device. The inflatable cuff may be deflated so that the artificial airway device may be more easily inserted into the patient, and thereafter inflated to anchor the artificial airway device in place.

In the method of insertion of an artificial airway according to the present invention, the inflatable cuff is first deflated. The artificial airway is lubricated, and then inserted down the patient's oral cavity. The seating tip of the artificial airway is fed along the hard and soft palate, the back of the oropharynx, and into the cricopharynx adjacent the cricoid. When resistance is felt due to interaction between the seating tip and the cricoid, insertion is halted. The artificial airway is then pulled back slightly, to lift the epiglottis away from the mask opening and so that the inflatable cuff is just behind the uvula. The inflatable cuff is then inflated. The patient may then be ventilated.

BRIEF DESCRIPTION OF THE DRAWINGS

Other objects and advantages of the invention will be apparent from the specification and claims, when considered in connection with the attached sheets of drawings, illustrating different forms of the invention, wherein like characters represent like parts and in which:

DESCRIPTION OF THE PREFERRED EMBODIMENTS

Figure 1:
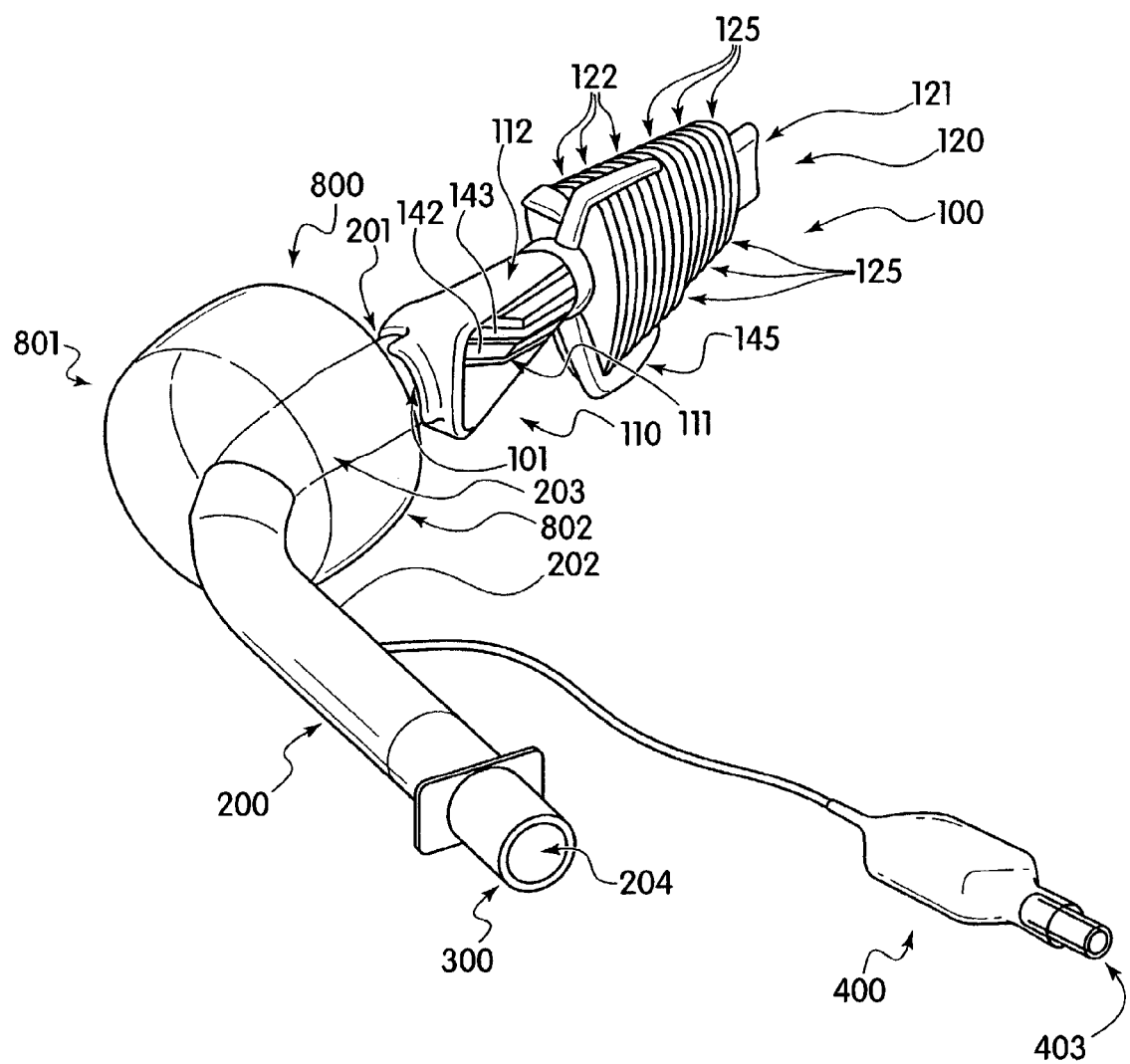
FIG. 1 is a perspective view of one embodiment of the artificial airway device of the present invention.

FIG. 1 is a perspective view of one embodiment of the artificial airway of the present invention. In the embodiment of FIG. 1, a mask portion 100 is connected to a partially curved airway tube 200 which includes a connection end 300. Connection end 300 may be connected to any known device or mechanism for providing artificial or spontaneous ventilation of a patient and/or for providing oxygen, air, anesthesia or other gases to the respiratory system of the patient. An inflation fluid supply unit 400 with a fluid connector 403 is also shown in FIG. 1.

In the embodiment shown in FIG. 1, the mask portion 100 includes a opening portion 110 and a seating tip 120 extending axially outwardly from the mask opening portion 110. The mask portion 100 is preferably integrally formed in one piece, and includes an opening 101 which securely receives a distal end 201 of the airway tube 200.

The airway tube 200 is assembled into the opening 101 and fixed to the mask portion 100, using any appropriate attachment technique or mechanism. In the preferred embodiment of FIG. 1, the airway tube 200 is made of a material which is sufficiently flexible to permit it to deform so as to fit down the patient's airway (see FIGS. 7 and 8), but is also sufficiently stiff to permit the airway tube 200 and the mask portion 100 to be accurately positioned manually in the patient P. Polyvinyl chloride (PVC), or any other known inexpensive, durable and partially flexible material may be used as the material from which the airway tube 200 is made.

The airway tube 200 includes a large central bore 204 through which various gases (e.g., anesthesia, oxygen, air) can be administered to the patient, if and when desired. In addition, the airway tube 200 includes a small conduit 202 in the tube wall. In the embodiment shown in FIG. 1, the small conduit 202 would be located on the underside (shown on the right in FIG. 1) of the airway tube 200. The small conduit 202 is used to transmit a fluid into and out of the interior of the inflatable cuff 800 to inflate and deflate the inflatable cuff 800, and is connected to the fluid supply unit 400.

Figure 7:
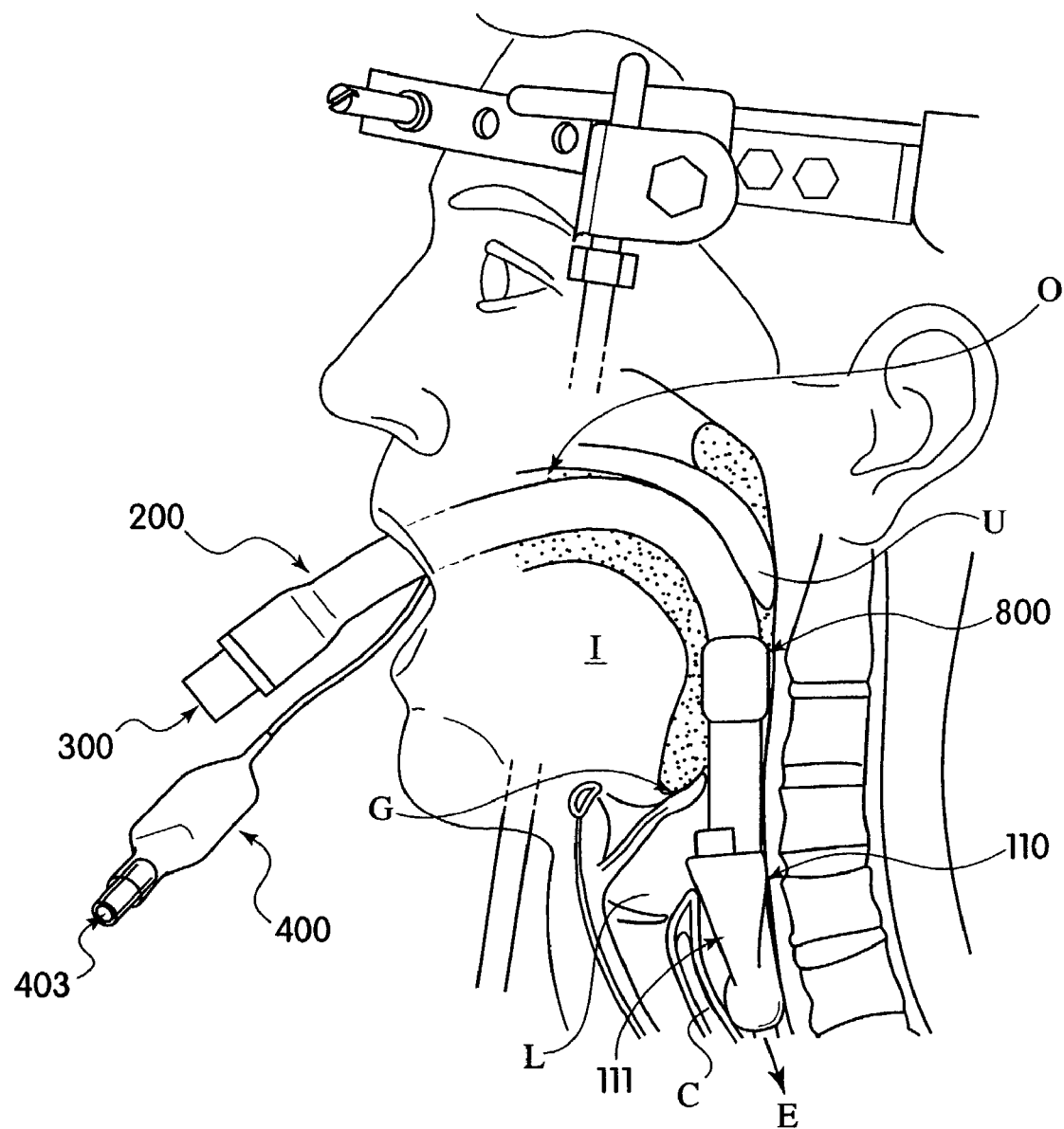
FIG. 7 is a partially cross-sectional view of the artificial airway device of the present invention, as inserted in the airway of a patient, prior to retraction and inflation.
Figure 8:
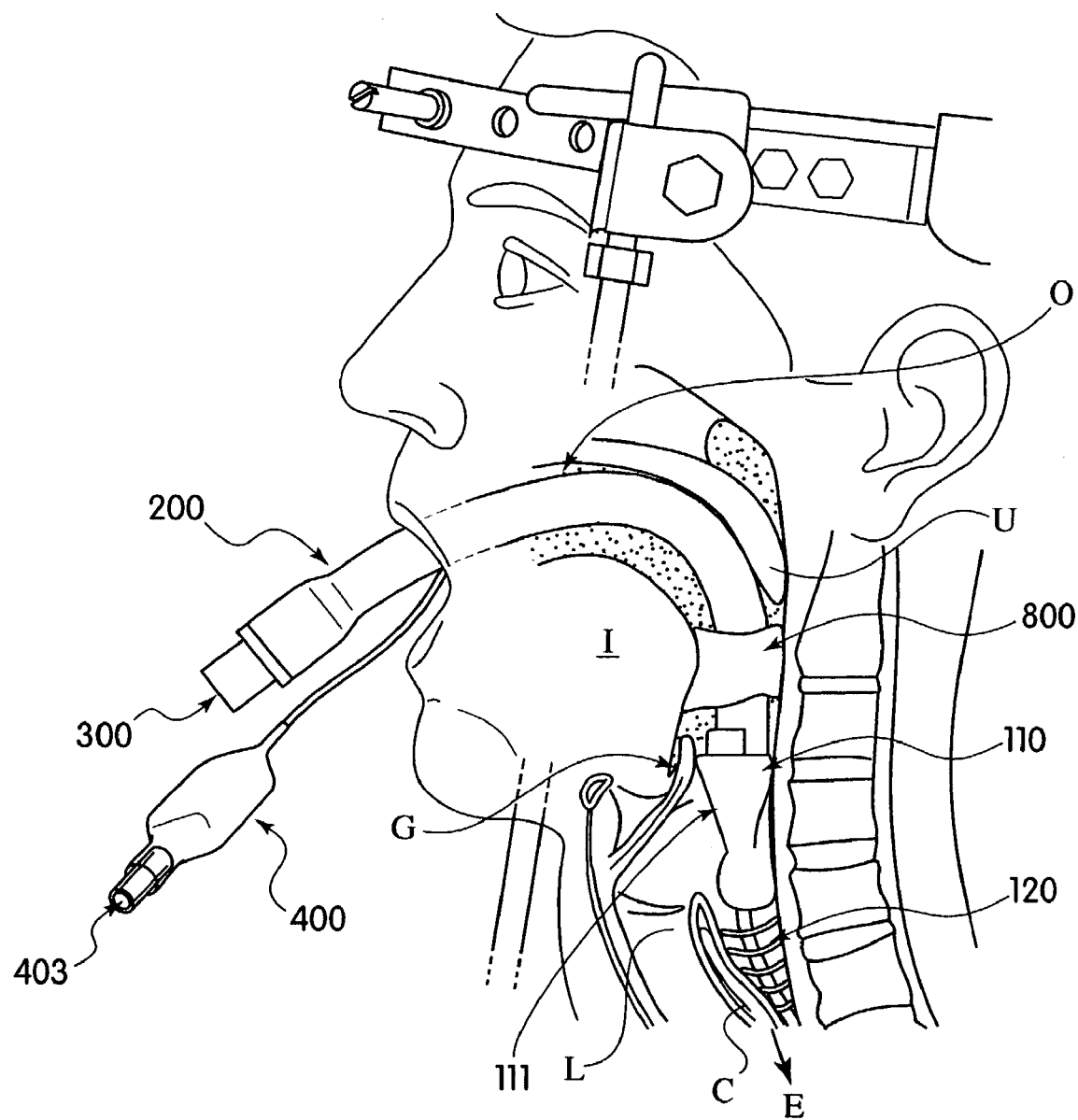
FIG. 8 is a partially cross-sectional view of the artificial airway device of the present invention, as inserted in the airway of a patient, after retraction and inflation.

The inflatable cuff 800, which is in the form of a fluid-expandable pillow or cuff, is mounted on the shaft of the airway tube 200, in a location on the tube 200 where it is adjacent the tongue T and behind the uvula U of the patient P in the pharynx when the mask opening portion 110 of the present invention is in place over the larynx L (see FIGS. 7 and 8). As shown in FIG. 1, the inflatable cuff 800 is offset relative to the airway tube 200, such that one side 801 of the inflatable cuff 800 extends a greater distance away from the airway tube 200 than the other side 802. The side 801 which extends a greater distance from the airway tube 200 is preferably located opposite the mask opening 111 of the mask opening portion 110. As a result, and as may be seen in FIG. 8, the mask opening portion 110 is located closely adjacent the laryngeal opening over the larynx L of the patient P when the artificial airway of the present invention is in place and the seating tip 120 is seated against the pharyngeal side of the cricoid C. During insertion of the artificial airway of the present invention into the airway of the patient P, the inflatable cuff 800 is in a contracted position (shown in FIG. 7). An opening 203 through the wall of airway tube 200 leads from the small conduit 202 to the interior of the inflatable cuff 800. Once the artificial airway of the present invention is in place with the mask opening portion 110 over the laryngeal opening of the larynx L, fluid may be applied to connector 403, thereby expanding the inflatable cuff 800 to the condition shown in FIG. 1. The inflatable cuff 800, in the expanded condition, contacts the tongue T of the patient P and the opposed portion of the oro-pharynx behind the uvula U, thereby anchoring the artificial airway of the present invention in place within the airway of the patient P.

The mask portion 100 includes an upper or proximal mask opening portion 110 and a lower or distal seating tip 120. The mask opening portion 110 includes a mask opening 111 which opens into the distal end 201 of the large conduit 204 in the airway tube 200, thereby allowing gases to be delivered to, and drawn from, the patient's respiratory system. The mask opening portion 110 has a shape 112 surrounding the mask opening 111 which is designed to approximate the shape of the laryngeal opening of the larynx L, thereby covering the laryngeal opening without sealing against the tissues surrounding the laryngeal opening. In this way, the mask opening portion 110 provides virtually complete coverage of the laryngeal opening of the larynx L, helping to prevent the incursion or ingress of anything into the patient's airway other than the gases delivered through the large conduit 204 of the airway tube 200.

The seating tip 120 includes a projecting finger 121 which extends from the mask opening portion 110 and a compressible structure surrounding the projecting finger 121. The projecting finger 121 is flexible, but is more rigid than the compressible structure mounted thereround. The compressible structure may preferably be formed by a plurality of axially spaced, thin fins or gills 122 and/or 125 extending radially outwardly from the projecting finger 121. The thin fins and/or gills 122 and/or 125 are relatively flexible in comparison with the projecting finger 121. Fins or gills 122 and/or 125 are preferably integrally molded with, and made of the same material as, the projecting finger 121. In a preferred embodiment, the entire mask portion 100 could be integrally molded in one piece from a durable biocompatible material such as urethane or polyvinyl chloride (PVC). The fins or gills 122 and/or 125 are designed so that they have a degree of flexibility, and thereby can be compressed or flexed to conform to the area above the esophagus E at the pharyngeal side of the cricoid C. The fins or gills 122 and/or 125 therefore conform and seat against the pharyngeal side of the cricoid C, and the associated area above the esophagus E opposite the pharyngeal side of the cricoid C, thereby anchoring the mask opening portion 110 in the area above the laryngeal opening of the larynx L.

Figure 2:
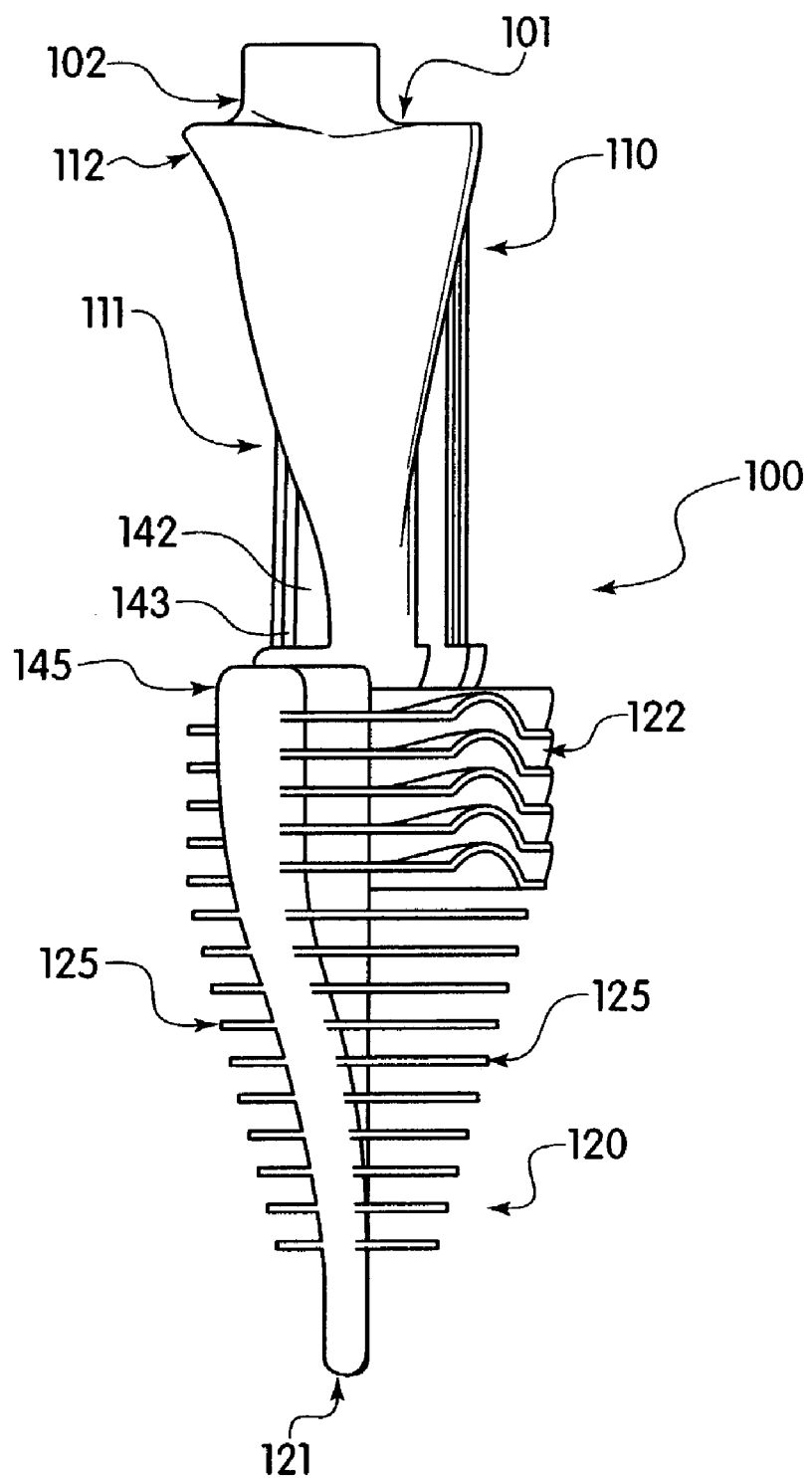
FIG. 2 is a side elevation view of the mask portion used with the embodiment of FIG. 1.
Figure 3:
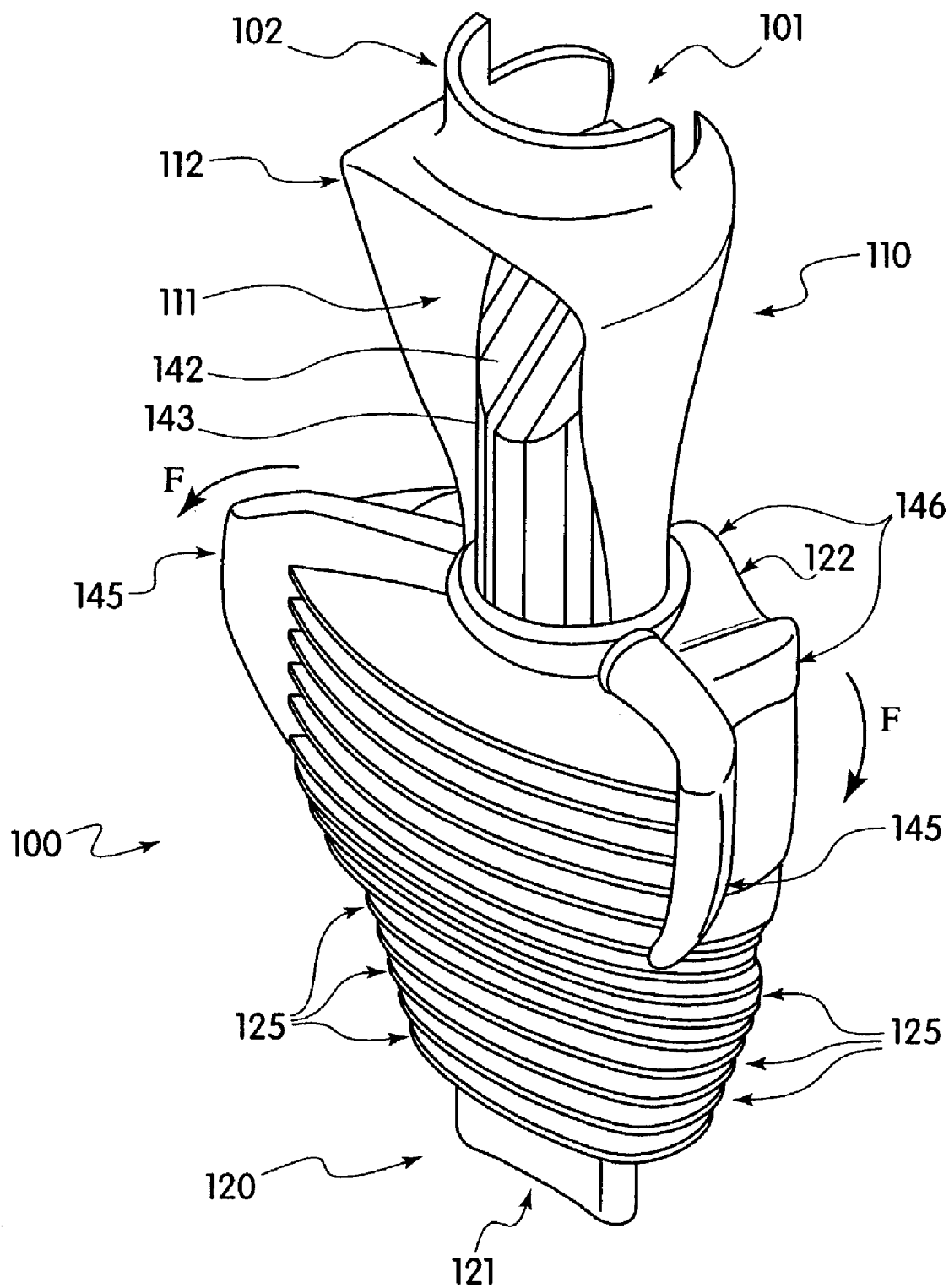
FIG. 3 is perspective view of the embodiment of FIG. 2.

FIGS. 2 and 3 show details of the mask portion 100 of FIG. 1. The mask portion 100 includes an upper or proximal mask opening portion 110 and a lower or distal seating tip 120. The mask opening portion 110 includes an opening 101 which connects with the large conduit 204 in the airway tube 200. A flange 102 may at least partially surround the opening 101 to assist in assembly of the distal end 201 of airway tube 200 to the mask portion 100. The mask opening portion 110 includes a mask opening 111 which connects the large conduit 204 of the distal end 201 of airway tube 200 to the laryngeal opening of the larynx L of the patient P. As shown in FIG. 3, the mask opening 111 is formed by a plurality of apertures 142 disposed in and through the surface of the mask opening portion 110. These apertures 142 are used to pass air, oxygen, anesthesia or other gases from the airway tube 200 through the mask portion 100 and into the patient's larynx L. The apertures 142 are separated from one another by a series of bars 143 forming a grate. The bars 143 act to restrain any anatomical portion, and in particular the epiglottis G, from entering into and blocking or partially blocking, the mask opening 111, thereby preventing obstruction of the delivery or removal of gases from the respiratory system of the patient P.

As shown in particular in FIG. 3, the mask opening portion 110 can be formed to have a shape 112 which is approximately trapezoidal, which shape 112 is designed to closely follow the shape of the laryngeal opening of the larynx L above which the mask opening portion 110 is placed. In this manner, the mask opening portion 110 serves to block the laryngeal opening of the larynx L from ingress of any material or object into the larynx L and respiratory system of the patient P, other than the gases which are delivered via the large conduit 204 of the airway tube 200.

In the mask portion of FIGS. 2 and 3, the seating tip 120 has a shovel-shaped design. As may be seen in FIG. 3, the fins and/or gills 122 and/or 125 taper in width from the proximal end to the distal end of the projecting finger 121. Two support arms 145 extend radially outward from the projecting finger 121. An extension of the arms 145 from the projecting finger 121 tapers from a maximum at proximal ends thereof toward distal ends thereof. As shown in FIGS. 1 and 3, the radial extension of a proximal portion 145a of each of the support arms 145 may preferably be greater than that of the corresponding proximal fins and/or gills 122 and/or 125. However, the angle of taper of the support arms 145 may be greater than that of the fins and/or gills 122 and/or 125 so that, the radial extension of the more distal fins and/or gills 122 and/or 125 exceeds that of the support arms 145. The support arm is preferably relatively rigid in comparison with the fins and/or gills 122 and/or 125. This is useful in nesting the device in the periform recesses and may assist in sealing and/or roationally anchoring the seating tip 120 in periform recesses. Of course, those skilled in the art will recognize that a certain degree of rotational play may be desired when the device is seated in the periform recesses. This desired amount of rotational play may be achieved by altering the size and/or rigidity of the support arms 145. Furthermore, the support arms 145 are preferably curved to conform to the shape of the periform recesses.

In addition, at least some of the fins or gills 122 and/or 125 on the side of the mask portion 100 which faces away from the larynx L have a curved shape which extends from one side of two support arms 145 projecting outwardly from the projecting finger 121. As shown in FIG. 2, at least some of the fins or gills 122 on the side of the mask portion 100 which faces away from the larynx L may also include undulations 146 across their width. These undulations 146 are used to compensate for flexing or expansion of the seating tip 120 in the direction F as the seating tip is inserted into, and conforms to, the area above the esophagus E where the pharyngeal side of the cricoid C is located and upon which the seating tip 120 seats. On the side of the support arms 145 opposite the fins or gills 122 are fins or gills 125. These fins or gills 125 preferably do not contain undulations, but instead compress as the seating tip flexes or expands in the direction F.

The shovel-shaped, tapered and flexible design of the embodiment shown in FIGS. 2 and 3 is preferable in that it can be used in a wide variety of patients, as the shape and flexibility of the seating tip 120 allows it to conform to, and seat in, many different sizes and shapes of patient airways and sizes and shapes of the area above the esophagus at the location of the pharyngeal side of the cricoid C where the seating tip 120 seats.

Figure 4:
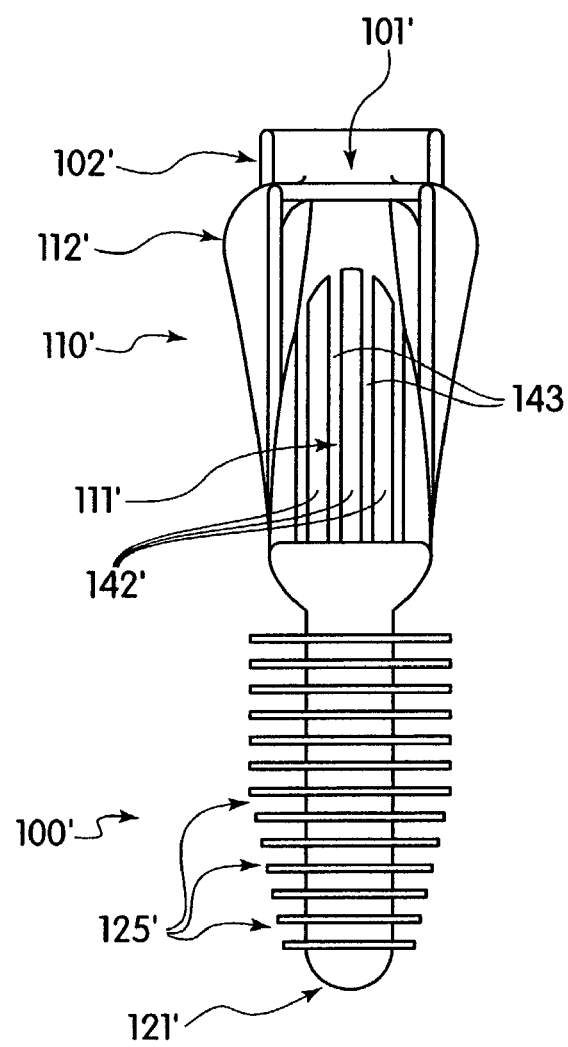
FIG. 4 is a rear elevation view of a second embodiment of a mask portion which may be used with the embodiment of FIG. 1.
Figure 5:
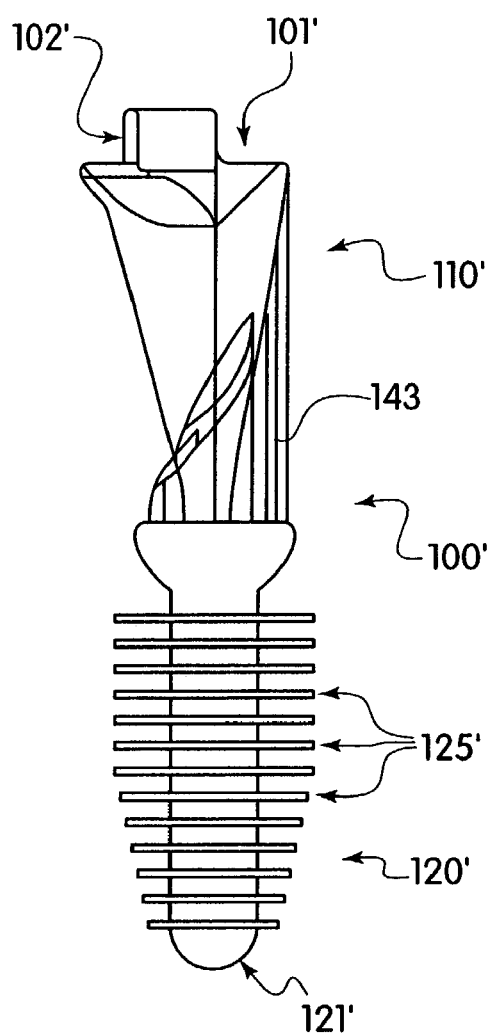
FIG. 5 is side elevation view of the embodiment of FIG. 2.

FIGS. 4 and 5 show an alternative, second embodiment of the mask portion 100' of the present invention. The embodiment of FIGS. 4 and 5, like the embodiment of FIGS. 1-3, includes an upper or proximal mask opening portion 110' and a lower or distal seating tip 120'. The mask opening portion 110' includes an opening 101' which connects with the distal end 201 of large conduit 204 in the airway tube 200. A flange 102' may at least partially surround the opening 101' to assist in assembly of the airway tube 200 to the mask portion 100'. The mask opening portion 110' includes a mask opening 111' which connects the large conduit 204 of the airway tube 200 to the laryngeal opening of the larynx L of the patient P. As shown in FIG. 4, the mask opening 111' is formed by a plurality of apertures 142 disposed in and through the surface of the mask opening portion 110' These apertures 142 are used to pass air, oxygen, anesthesia or other gases from the airway tube 200 through the mask portion 100' and into the patient's larynx L. The apertures 142 are separated from one another by a series of bars or grates 143. The bars or grates 143 act to restrain any anatomical portion, and in particular the epiglottis G, from entering into and blocking or partially blocking, the mask opening 111', thereby preventing obstruction of the delivery or removal of gases from the respiratory system of the patient P.

As shown in FIG. 3, upper portions of at least some of the bars 143 may preferably form an angled surface 143a which will assist in the insertion of any tube into the larynx via the airway tube 200. That is, a tube threaded down the airway tube 200 will contact the angled portion 143a and be turned away from the axis of the airway tube 200 with the angle of the angled surface 143a chosen to point toward the larynx when the device is in the desired seating position. That is, the optimum angle between bars 143 and the angled surface 143a changes based on position of mask opening relative to laryngeal opening, with greater angles being more suitable for higher placements of the mask opening relative to the laryngeal opening. This angle is preferably in the range 10° to 60°, and is most preferably approximately 30°. Of course, as shown in FIG. 5, the angled surface 143a may be radiused and/or have a proximal end parallel to the conduit axis to further assist in the insertion of tubes into the laryngeal opening. In addition, the angled surface 143a may be formed entirely separately from the bars 143, so long as the surface is aimed toward the laryngeal opening when the device is in the operative position. In addition, the apertures 142 between the bars 143 increase the likelihood of establishing a ventilation path even when substantial mucousa is present.

Furthermore, those skilled in the art will understand that the bars 143 need not extend distally to proximally as shown in FIG. 3. Rather, the bars 143 may extend in any direction within the mask opening 111 so long as suitable channels 142 are formed therebetween. For example, if the bars 143 extend substantially perpendicular to the axis of the airway tube 200, channels 142 will also extend substantially perpendicular to the axis of the airway tube 200. These channels 142 may communicate with the airway tube 200 through an interior passage passing behind the bars 143. Then the angled surface 143a would be formed on a proximal surface of a proximal-most one of the bars 143.

As shown in particular in FIG. 4, the mask opening portion 110' can be formed to have a shape 112' which is approximately trapezoidal, which shape 112' is designed to closely follow the shape of the laryngeal opening of the larynx L above which the mask opening portion 110' is placed. In this manner, the mask opening portion 110' can serve to block the laryngeal opening of the larynx L from the ingress of material or any other object into the larynx L and respiratory system of the patient P, other than the gases which are delivered via the large conduit of the airway tube 200.

Figure 6:
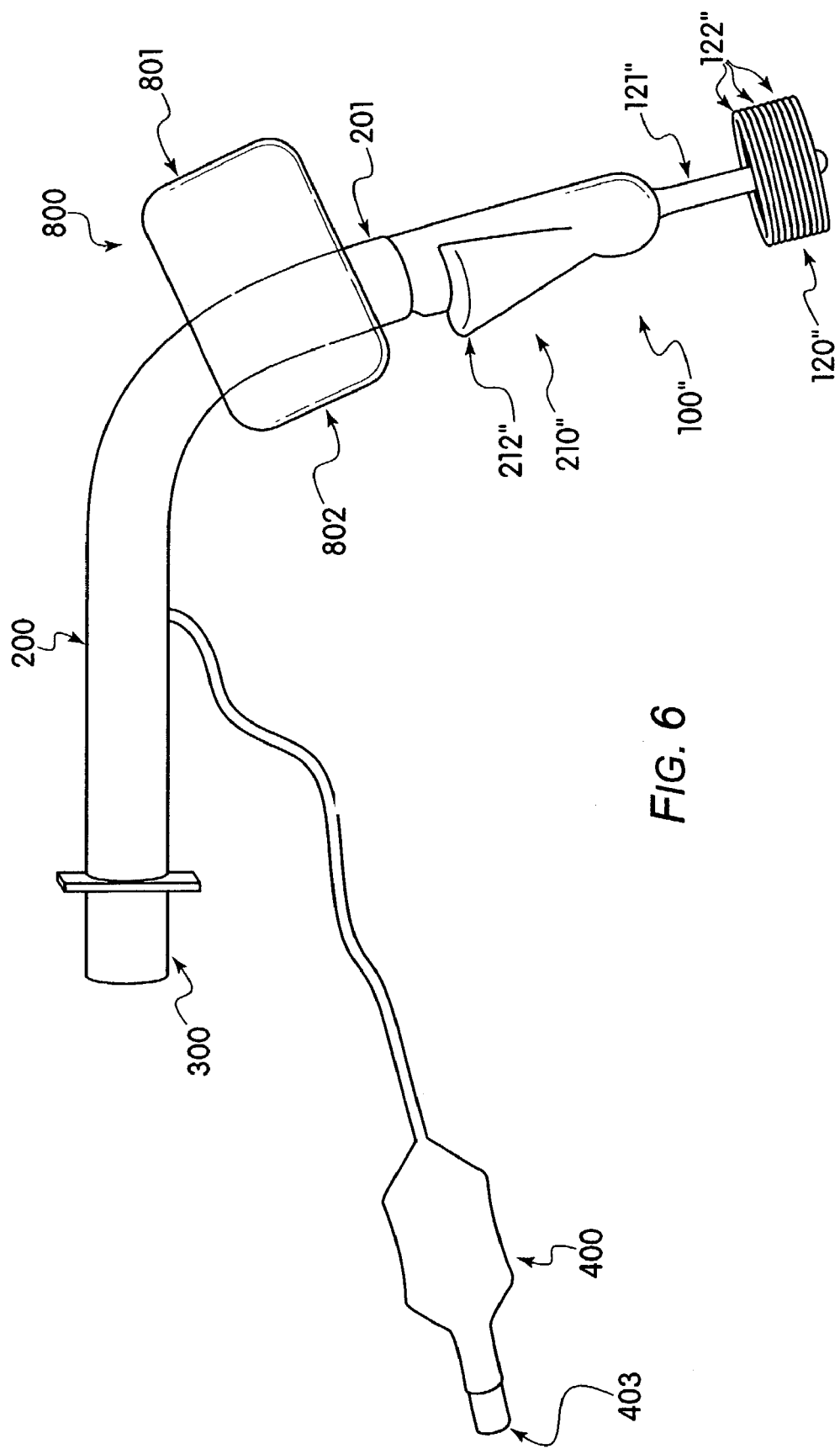
FIG. 6 is a side elevation view of a third embodiment of a mask portion used with airway device of FIG. 1.

FIG. 6 shows an additional embodiment of the mask portion 100", which includes a modified configuration of the fins or gills 122" and projecting finger 121" of the seating tip 120", as well as a slightly different configuration of the shape 112" and the mask opening portion 110". The operation of the embodiment of FIG. 6, however, is identical to the embodiments described above.

FIG. 7 shows the artificial airway of the present invention in place in a patient P, with the inflatable cuff 800 uninflated, and in place adjacent the tongue T and the portion of the oro-pharynx near the uvula U, but prior to retraction. FIG. 8 shows the artificial airway in place in a patient P, after retraction and inflation of the inflatable cuff 800. As shown in FIG. 8, the artificial airway of the present invention, and in particular the mask opening portion 110, seats properly in place above the laryngeal opening L of the patient P. As may also be seen in FIG. 8, the seating tip 120 seats in the area above the entrance to the esophagus E against the pharyngeal side of the cricoid C and the portion of the pharynx opposite the pharyngeal side of the cricoid C.

Operation of the various embodiments and methods of their use will now be described, with reference to FIGS. 7 and 8. The patient's P mouth is opened and the seating tip 120, airway tube 200 and inflatable cuff 800 are lubricated for ease of insertion. The artificial airway of the present invention is inserted down the oral cavity O with the mask opening 111 facing toward the tongue T during insertion. The airway tube 200 is pushed inwardly into the oral cavity O and the seating tip 120 is fed along the hard and soft palate, the back of the oropharynx, and into the cricopharynx adjacent the cricoid C. When resistance is felt due to interaction between the seating tip and the pharyngeal side of the cricoid C above the entrance to the esophagus E, insertion is halted. That position is shown in FIG. 7. Once the seating tip 120 seats against the pharyngeal side of the cricoid C, the individual inserting the artificial airway of the present invention will feel the seating tip 120 seating, and therefore will know that the artificial airway of the present invention is properly in place. The airway tube 200 may then be retracted or pulled back slightly outwardly, so that the mask opening portion 110 pushes the epiglottis G up and away from the mask opening 111, as shown in FIG. 8. Thereafter, the inflatable cuff 800 is expanded by applying fluid under pressure to connector 403, which fluid travels down the small conduit of the airway tube 200 and enters the interior of inflatable cuff 800 to expand inflatable cuff 800 until it contacts the tongue T and the opposed portion of the oro-pharynx behind the uvula U, thereby securing the artificial airway of the present invention in place. That condition is also shown in FIG. 8. Once the artificial airway is in place, any mechanism or structure which is used for the delivery of gases to the respiratory system of the patient may be connected to connection end 300, or the connection end could be left free to allow spontaneous ventilation by the patient P.

Thus, there is shown and described a unique design and concept of an artificial airway and method of its use and insertion. While this description is directed to particular embodiments, it is understood that those skilled in the art may conceive modifications and/or variations to the specific embodiments shown and described herein. Any such modifications or variations which fall within the purview of this description are intended to be included as part of the invention. It is understood that the description herein is intended to be illustrative only and is not intended to be limitative. Rather, the scope of the invention described herein is limited only by the claims.

What is claimed is:

1. An artificial airway device comprising:
an air conduit extending between a proximal opening and a mask opening wherein, when the device is in an operative position, the proximal opening remains outside of a patient and the mask opening is open to a laryngeal opening of the patient;
a seating tip extending distally from the distal end of the air conduit which, when the device is in the operative position, is located on a pharyngeal side of a patient's cricoid;
a first supporting arm that extends axially along the seating tip in a shape substantially corresponding to that of a portion of the esophagus contacting the first supporting arm when the device is in the operative position; and
at least one bar extending within the mask opening;
wherein the at least one bar comprises a plurality of bars separated from one another to form at least one channel in the mask opening; and
wherein the at least one channel fluidly communicates with the air conduit.

2. An artificial airway device comprising:
an air conduit extending between a proximal opening and a mask opening wherein, when the device is in an operative position, the proximal opening remains outside of a patient and the mask opening is open to a laryngeal opening of the patient;
a seating tip extending distally from the distal end of the air conduit which, when the device is in the operative position, is located on a pharyngeal side of a patient's cricoid;
a first supporting arm that extends axially along the seating tip in a shape substantially corresponding to that of a portion of the esophagus contacting the first supporting arm when the device is in the operative position; and
at least one bar extending within the mask opening;
wherein the at least one bar comprises a plurality of bars separated from one another to form at least one channel in the mask opening; and
wherein the at least one bar extends in a substantially distal to proximal direction.

3. An artificial airway device comprising:
an air conduit extending between a proximal opening and a mask opening wherein, when the device is in an operative position, the proximal opening remains outside of a patient and the mask opening is open to a laryngeal opening of the patient;
a seating tip extending distally from the distal end of the air conduit which, when the device is in the operative position, is located on a pharyngeal side of a patient's cricoid;
a first supporting arm that extends axially along the seating tip in a shape substantially corresponding to that of a portion of the esophagus contacting the first supporting arm when the device is in the operative position; and
at least one bar extending within the mask opening;
wherein the at least one bar comprises a plurality of bars separated from one another to form at least one channel in the mask opening; and
wherein the at least one bar extends in a direction substantially perpendicular to a distal to proximal direction.

4. An artificial airway device comprising:

an air conduit extending between a proximal opening and a mask opening wherein, when the device is in an operative position, the proximal opening remains outside of a patient and the mask opening is open to a laryngeal opening of the patient;

a seating tip extending distally from the distal end of the air conduit which, when the device is in the operative position, is located on a pharyngeal side of a patient's cricoid;

a first supporting arm that extends axially along the seating tip in a shape substantially corresponding to that of a portion of the esophagus contacting the first supporting arm when the device is in the operative position;

at least one bar extending within the mask opening; and a tube directing surface extending within the mask opening, the tube directing surface being oriented so that, when the device is in the operative position, a plane of the tube directing surface extends to the laryngeal opening of the patient so that a tube inserted through the airway conduit to the tube directing surface is aimed by the tube directing surface into the laryngeal opening.

5. The artificial airway device of claim 4, wherein the tube directing surface has a radiused portion with the plane being tangent to a distal end of the radiused portion.

6. The artificial airway device of claim 5, wherein a proximal end of the tube directing surface is substantially parallel to an axis of the air conduit.

7. An artificial airway device comprising:

an air conduit extending between a proximal opening and a mask opening wherein, when the device is in an operative position, the proximal opening remains outside of a patient and the mask opening is open to a laryngeal opening of the patient;

a seating tip extending distally from the distal end of the air conduit which, when the device is in the operative position, is located on a pharyngeal side of a patient's cricoid;

a first supporting arm that extends axially along the seating tip in a shape substantially corresponding to that of a portion of the esophagus in which the seating tip is located when the device is in the operative position; and a tube directing surface extending within the mask opening, the tube directing surface being oriented so that, when the device is in the operative position, a plane of the tube directing surface extends to the laryngeal opening of the patient so that a tube inserted through the airway conduit to the tube directing surface is aimed by the tube directing surface into the laryngeal opening, wherein the tube directing surface is formed by a portion of at least one bar extending within the mask opening.

* * * * *